United States Patent [19]

Clendenning

[11] 3,933,592

[45] Jan. 20, 1976

[54] METHOD OF DETECTING LIVING MICROORGANISMS

[75] Inventor: John R. Clendenning, Washington, D.C.

[73] Assignee: Hazleton Laboratories, Incorporated, Vienna, Va.

[22] Filed: Oct. 5, 1970

[21] Appl. No.: 78,241

Related U.S. Application Data

[63] Continuation of Ser. No. 433,488, Feb. 17, 1965, abandoned.

[52] U.S. Cl. .......................................... 195/103.5 R
[51] Int. Cl.² .......................................... C12K 1/04
[58] Field of Search ................................. 195/103.5

[56] References Cited
UNITED STATES PATENTS
2,905,592   9/1959   Shull et al. ........................... 195/104

OTHER PUBLICATIONS

Franzen et al., The Journal of Biological Chemistry Vol. 236 No. 2 pp. 515–519 (Feb. 1961).

Strehler et al. Methods in Enzymology Vol. III pp. 871–873 (1957).

Frobisher, Fundamentals of Microbiology 7th Ed. pp. 299, 300, 328 and 329 (1962).

Ormsbee et al., Journal of Immunology Vol. 88 pp. 741–749 (1962).

*Primary Examiner*—Alvin E. Tanenholtz
*Attorney, Agent, or Firm*—Laurence, Stokes & Neilan

[57] ABSTRACT

The presence or absence of living microorganisms is determined by treating a sample containing said microorganisms with an adenosine triphosphate reactive mixture containing luciferin, luciferase and a cation in the presence of oxygen and measuring the light emission produced.

18 Claims, No Drawings

METHOD OF DETECTING LIVING MICROORGANISMS

CROSS-REFERENCE TO RELATED APPLICATION

This application is a continuation of Ser. No. 433,488 filed Feb. 17, 1965, now abandoned.

This invention relates to a rapid method for detecting the presence or absence of a living organism. More particularly, this invention relates to a method for rapidly determining whether a sample of material contains any living organisms.

There exists a need for a method of rapidly detecting the existence of living organisms in a particular environment. This need is particularly acute in those areas where it is necessary to determine quickly the existence of microorganisms. Such areas include, for example, the detection of biological warfare agents; the determination of background levels of microorganisms in the environment such as air, water, food, clean assembly areas, hospital rooms and germ-free areas, and the detection of any increased contamination in any of these environments; and monitoring the effectiveness of sterilization procedures and the sterilization of compounds and apparatus.

It is an object of this invention to provide a method for rapidly detecting the presence or absence of living organisms in a given environment.

It is another object of this invention to provide a method for the detection of biological warfare agents.

It is a further object of this invention to provide a means for the determination of background levels of microorganisms in air, water, food, hospital rooms, sterile areas, etc., and for the detection of any increased contamination in any of these environments.

It is still another object of this invention to provide a method for monitoring the effectiveness of sterilization procedures.

These and other objects are attained by the practice of this invention which, briefly, comprises mixing in the presence of oxygen a sample of the environment to be tested or assayed for living organisms, such as an aqueous extract of a material which is suspected to contain living organisms, with firefly lantern extract which includes a mixture comprising luciferin, luciferase and a cation such as magnesium. If living organisms are present in the sample, this fact will be indicated by the emission of light. This emission of light is caused by the reaction of adenosine triphosphate (hereinafter referred to as ATP), which is present in all living organisms, with the constituents of the firefly lantern extract in the presence of oxygen. Thus, the practice of this invention utilizes the phenomenon of firefly bioluminescence to establish the presence of living organisms by the reaction of ATP with firefly lantern extract. The amount of bioluminescent light which is emitted is directly proportional to the amount of ATP in the material tested.

The reactants required for firefly bioluminescence are the substrate, luciferin; the enzyme, luciferase; the activator, ATP; a cation (usually magnesium); and oxygen. The overall reaction is an oxidation reaction catalyzed by the enzyme, luciferase, which results in the emission of light. A general mechanism of the course of the reaction is as follows:

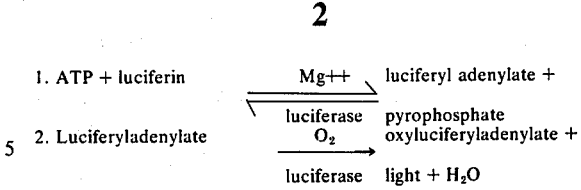

This reaction is absolutely specific for ATP. The ATP may not be replaced by any other known compound.

The firefly bioluminescent reaction may be carried out utilizing crude firefly lantern extracts or the purified constituents therefrom which participate in the bioluminescent reaction. It has been found that a sufficiently high degree of sensitivity may be attained using the primary extract of the firefly lantern.

Lyophilized firefly lantern extract may be obtained commercially. This material may be prepared for use by dissolving it in distilled, deionized water to the desired concentrations. The extracts used in the examples which follow, unless otherwise specified, were obtained by dissolving 70 mg. of lyophilized firefly lantern extract in 5 ml. of water. The lyophilized preparation also contains $MgSO_4$ and potassium arsenate in amounts sufficient to result in concentrations of 0.01M and 0.05M, respectively. The pH of such a solution is 7.4. The solutions may be further diluted to give any desired concentration of firefly lantern extract.

The firefly lantern extract which may be used in the practice of this invention may also be prepared in the laboratory from dessicated firefly tails. The firefly tails are first ground to a fine powder with a mortar and pestle with a small amount of washed silica. The powder is then extracted with 0.05M potassium arsenate - 0.01M $MgSO_4$ at pH 7.4.

When crude firefly lantern extract is used in the practice of this invention, there may be present in the extract small amounts of ATP and ATP precursors, along with phosphorylating enzymes capable of converting the precursors into ATP. The presence of these materials may give rise to a basal light emission by the firefly extract in the absence of exogenous ATP. This type of light emission, which is referred to as inherent light, occasionally may interfere with the detection of light emission in the practice of this invention. However, the problem of inherent light may be eliminated or minimized by one or more of the following techniques:

1. The firefly extract may be partially purified to remove the factors responsible for the inherent light. The separation and partial purification of luciferase and luciferin is described by McElroy (*Methods in Enzymology*, Vol. II, page 851, Academic Press, Inc., New York, 1955).

2. Another approach to the removal of inherent light involves the "salting out" of luciferase by the addition of ammonium sulfate to the firefly extract, leaving the nonprotein factors responsible for inherent light in the supernatant. This has been accomplished as follows: 50 mg. of lyophilized extract were suspended in 10 ml. of 2.7 M ammonium sulfate. After standing at room temperature for 15 minutes, the suspension was centrifuged at approximately 200 G for 10 minutes after which the supernatant was discarded. The precipitate, after being washed twice with 10 ml. aliquots of 2.7 M ammonium sulfate, was taken up in 2.5 ml. of a solution of 0.05 M potassium arsenate buffer (pH 7.4) and 0.01M magnesium sulfate. This treatment, followed by reconstitution with partially purified luciferin, reduces the overall activity of the extract by only about 15% and reduces the inherent light by about 90%.

3. Experiments have indicated that the use of calcium phosphate gel will also reduce the inherent light in the extract without significantly reducing the activity of the extract. Thus, 50 mg. of commercial lyophilized firefly extract were dissolved in 1.25 ml. of deionized water and centrifuged. The solution was then treated from one to three times with varying amounts of calcium phosphate gel (from 249 mg. to 334 mg.). The treatment consisted of shaking the gel with the extract for ten minutes and then removing the gel by centrifugation at 200 G for 10 minutes. With one treatment with calcium phosphate gel, there is a reduction of about 85% of the inherent light with only a loss of from 7 to 26% of luciferin - luciferase activity.

4. The simplest means for reducing the inherent light is by dilution of the extract with water. Maximum sensitivity with the least amount of inherent light is obtained at a lyophilized extract concentration of 3 mg./ml.

Since ATP is ubiquitous in all living organisms, the practice of this invention may be used to determine rapidly the presence of any living organisms present in minute quantities. Using electronic equipment, living organisms containing an amount of ATP less than $2\times10^{-4}$ ug. and approaching $10^{-7}$ ug. may be detected. The bioluminescent reaction itself takes less than 0.5 second to attain maximum amplitude. In calibration experiments with pure cultures of microorganisms, it has been possible to detect as few as 100 cells of *Saccharomyces cerevisiae* and 6000 cells of *Serratia marcescens*.

The practice of this invention may be used to detect the presence of bacterial cells. Although nonviable cells may themselves contain ATP and therefore register a positive bioluminescent response, this apparent difficulty can be overcome by making an initial quantitative determination of the bioluminescent light emitted by a cell sample. The sample is then incubated in a suitable media for a short while and again is tested and a quantitative determination of the bioluminescent light emitted by the incubated sample determined. If there is an increase in the amount of bioluminescence between the incubated cell sample and the unincubated cell sample, this will establish the presence of viable cells or bacteria in the sample. Using this procedure it is possible to make determinations of specific bacteria by selection of an appropriate incubation media and environment that would favor the growth of a specific microorganism.

The practice of this invention may be used to determine the particular antibiotic which will be most effective in the treatment of a bacterial infection. A suitable nutrient media for the bacteria is divided into several equal aliquots and a different antibiotic is added to each aliquot. The aliquots are then inoculated with the bacteria, incubated and assayed for ATP by the firefly bioluminescent reaction. The aliquot which exhibits the least increase in ATP content following incubation indicates that the particular antibiotic contained in that aliquot is the most effective in inhibiting the growth of the bacteria. This technique may also be used to determine the optimum concentration of the antibiotic for inhibiting the bacteria.

The specific type of bacteria may be determined by providing equal aliquots of the nutrient media and adding a different vaccine or antibody, each of which is specific for a different bacteria, to each aliquot. Each aliquot is then inoculated with the bacteria. Following a suitable incubation period, the aliquots are assayed for ATP content. If the results show that one tissue culture has not undergone a significant increase in ATP content, the unknown bacteria will be identified as the one for which the vaccine or antibody contained in that tissue culture is specific.

The practice of this invention may also be used to detect rapidly the presence of microorganisms in water, for example. Since the level of intensity of bioluminescent light emitted from a sample containing microorganisms is directly proportional to the amount of ATP and hence indicative of the number of organisms present in the test portion, this method may be used to monitor the quality of public water supplies. Whereas at the present time, from 48 to 72 hours are commonly required to obtain the results of bacteriological examinations, this invention permits results to be obtained in a matter of minutes.

This invention may also be applied to samples obtained in conventional fashion from air or other sources which are suspected of containing living material.

Comparisons of ATP content may be made on the basis of ATP per unit volume of material tested or ATP per unit protein weight or both.

In assaying cells, qualitative results may be obtained by mixing intact cells or tissues with the firefly lantern extract. That is, whole cells or tissues may be used to determine a positive or negative response in the bioluminescent test for the presence of living organisms. However, for maximal response and in order to make accurate quantitative assays, it is preferred to rupture the cells and extract the ATP therefrom. A variety of methods for the extraction of ATP from cells may be used. These include hot water extraction, acetone extraction, ultrasonic disruption, dimethylsulfoxide extraction and perchloric acid extraction. Some of the methods which may be used for accomplishing rupture and extraction of the cells are described below:

A. Acetone and hot water: ONe ml. of the washed cell suspension is added to 10 ml. of deionized water and the suspension maintained at 100°C for 1 to 5 minutes. The preparation is then cooled and assayed for ATP.

The acetone extraction consists of adding one ml. of a washed cell suspension to 10 ml. of acetone. After standing for 1 to 5 minutes, a one ml. aliquot of the mixture is taken to dryness in air and the residue suspended in one ml. of deionized water. The preparation is then assayed.

B. Dimethyl Sulfoxide (DMSO): DMSO is a high-boiling point organic solvent, miscible with water in all proportions and exhibiting a very low order of toxicity. One ml. aliquots of a bacterial cell suspension are added to 10 ml. of various concentrations of DMSO in water. After standing for 5 minutes, the suspension is assayed for ATP response.

C. Ultrasonic Oscillation — Ultrasonic oscillation has been successfully used by many investigators for the rupture of microbial cells. Five ml. of bacterial suspension are subjected to 1 to 5 minutes of ultrasonic oscillation at 50 to 75 watts. After cooling the tube in flowing water, the treated suspension is assayed for ATP response. Trichloroacetic acid (0.5 ml. of 5% solution) may be added to the cell suspension prior to sonication in order to stabilize the ATP against hydrolysis.

D. Perchloric Acid: Up to 0.2 ml. of perchloric acid may be added to 5 ml. of washed cell suspension. The preparation is then assayed.

It is preferred to contact the material to be tested and the firefly lantern extract in a liquid reaction medium, such as sterile, deionized water. The liquid reaction medium will generally contain enough dissolved oxygen to allow the bioluminescent reaction to take place.

The material to be assayed should be mixed with the firefly lantern extract in a manner which permits the visual observation and/or mechanical measurement and recordation of the light emitted. When visual screening is employed, the test is desirably carried out in a dark room. Only qualitative results can practically be determined using visual screening — i.e., whether or not light is emitted indicating a positive or a negative response for the presence of living organisms.

Examples 1 to 11, below, demonstrate the use of visual screening to assay cultures for living organisms.

EXAMPLES 1 to 11

In these examples, visual screening of microorganisms is employed for determining a response to the firefly luminessence system. Each test is carried out in a dark room after a period of dark adaptation is achieved by wearing fluoroscopy goggles prior to testing the organisms. Cultures of the micro-organisms listed below are assayed. The incubation broth containing each culture is centrifuged and the supernatant is discarded. The recovered cells are resuspended in 1.0 ml. of deionized water and centrifuged again. The supernatant is discarded, the cells are resuspended in 1.0 ml. of deionized water and placed in a boiling water bath for 10 minutes. The preparation is then centrifuged and 0.1 ml. of the supernatant is added to a mixture of 1.0 ml. of 0.025 M glycylglycine buffer (pH 7.5), 0.05 ml. of 0.1 M $MgSO_4$, and 0.05 ml. of firefly lantern extract (prepared by adding 50 mg. of dry firefly lanterns to about 4 ml. of water, centrifuging the mixture for 10 minutes at 1,700 G and recovering the supernatant). Positive responses are obtained (i.e., the emission of light was observed) with the following microorganisms:

| Example | Microorganism |
|---------|---------------|
| 1 | Saccharomyces cerevisiae |
| 2 | Azotobacter agilis |
| 3 | Pseudomonas fluorescens |
| 4 | Bascillus cereus |
| 5 | Streptomyces bobiliae |
| 6 | Staphylococcus epidermis |
| 7 | Arthrobacter simplex |
| 8 | Bacillus subtilis |
| 9 | Xanthomonas campestris |
| 10 | Micrococcus cinnabareus |
| 11 | Xanthomas beticola |

In order to observe and record small amounts of light produced by a positive response between the material to be assayed and the firefly lantern extract and to make quantitative measurements of the amount of light emitted, it is preferred to make use of instruments or an apparatus which will sense and record the intensity of the emitted light.

When instruments are used to detect and record the intensity of emitted light, the procedure consists of injecting a liquid medium containing the material to be assayed for living organisms, such as an aqueous extract of the material, into a cuvette containing the firefly lantern extract. The extract is held at pH 7.4 with potassium arsenate buffer. The light emitted as the result of the reaction between any ATP in the material to be tested and the firefly lantern extract strikes the surface of a photomultiplier tube giving rise to a current which can be measured and recorded by either an oscilloscope photograph or a linear recorder. The unit of intensity used for comparing these reactions is the millivolt. In this application, the unit of light intensity has been arbitrarily defined as being equivalent to one millivolt. Alternately, a pulse counting device with a digital or analogue read-out may be used to record the reaction.

Because the response (i.e., light emission) is almost instantaneous when a living organism is contacted with the firefly lantern extract, the extract should be positioned in front of the light detection system prior to the introduction of the material to be assayed.

There are two ways in which the bioluminescent response with ATP present in a material can be expressed. One is by measurement of the maximum intensity of the emitted light, which after reaching this maximum value, decays exponentially. With all other factors constant, the maximum intensity is directly proportional to the concentration of ATP. The alternative manner of expressing the response is by integration of the total amount of light emitted; i.e., area under the light intensity curve. This is the slower of the two methods, because of the relatively long time necessary for complete decay (up to 10 minutes). Therefore, maximum intensity has been chosen as the measure of ATP response.

The instrumentation necessary for the quantitative measurement of bioluminescence consists of a photomultiplier tube for the conversion of light energy into an electrical signal, a device for determining the magnitude of the signal, and a light tight chamber for presentation of the bioluminescent reaction to the photomultiplier tube.

In one system, part of the assembly consists of a composite sensing and reaction chamber which contains a photomultiplier tube, with appropriate circuitry, and a rotary cylinder mounted in a block of aluminum in a manner which permits removal of the reaction chamber without exposing the phototube to light. A section of the cylinder wall is cut out to accommodate a standard ten mm or five mm rectangular cuvette. Immediately above the cuvette holder is a small injection port sealed with a replaceable light-tight rubber plug. The entire unit is painted black to reduce light reflection. The photomultiplier converts the light energy into an electrical signal. An oscilloscope, which records the magnitude of the signal from the photomultiplier, is provided with a maximum sensitivity of 200 uv/cm of beam deflection which will allow an increase in system sensitivity by decreasing the bandwidth or directly reducing the noise level. There is a multiple switching arrangement at the scope input which makes it convenient to adjust the system zeros and balances. The differential input to the scope provides a means to balance the dark current output of the phototube. The response to the firefly luminescent system displayed on the oscilloscope screen is recorded with a camera which mounts directly onto the front of the oscilloscope. To observe and record the reaction, the cuvette containing the necessary reagents is positioned in the cuvette carrier without exposing the phototube. Rotation of the carrier positions the cuvette in front of the phototube. The unknown is then added through the injection port and the magnitude of the response, if any, is recorded by the camera.

A typical procedure for assaying an unknown material according to the practice of this invention utilizing electronic apparatus to detect and record the intensity of the bioluminescent reaction is described below:

PROCEDURE A

One ml. of a 0.5% buffered aqueous solution of commercially available lyophilized firefly lantern extract is placed into a cuvette which is then positioned in the light detection chamber of the type previously described. The extract contains luciferase, luciferin and magnesium. Sufficient dissolved oxygen for the bioluminescent reaction is present in the solution. An aqueous suspension of material suspected to contain living organisms is subjected to ultrasonic vibration for one or more minutes. One tenth ml. of the suspension is then drawn into a hypodermic syringe and immediately injected through the light-proof seal into the cuvette. The reaction reaches maximum light intensity in less than 0.5 seconds and then decreases exponentially for several minutes. The entire procedure can be executed and the response through its maximum amplitude recorded in less than 2 minutes.

In order to make quantitative determinations of the amount of ATP present, the instrument used to measure the light response may be calibrated using known concentrations of ATP. A calibration may be plotted by injecting 1/10 ml. portions of known concentrations of ATP through the light-proof seal into the cuvette by means of a hypodermic syringe. The light response in millivolts is plotted against the ATP concentration. A straight linear function is obtained. For example, if the response from $10^{-1}$ gamma of ATP is 20,000 millivolts, that from $10^{-2}$ is 2000 millivolts, etc.

The following examples illustrate the use of an apparatus as previously described for screening the materials for the presence of living organisms:

EXAMPLE 12

Glycylglycine buffer (1.0 ml.) and firefly lantern extract (0.1 ml.) are placed into a rectangular, 5 mm., quartz cuvette which is then positioned in front of a phototube. A broth culture of *Escherichia coli* is injected into the reaction chamber through a light tight port, by using a 20 gauge needle and a 0.25 ml. syringe. The apparatus recorded a response of greater than 75 mv.

EXAMPLE 13

The process of Example 12 is repeated except that the cell culture is heated in a boiling water bath for 10 minutes before it is injected into the reaction chamber. The apparatus recorded a response of 700 mv.

EXAMPLE 14

The process of Example 12 is repeated except that before testing, the cell culture is centrifuged for about 10 minutes at 1,700 G, the supernatant is discarded, and the cells are resuspended in about 0.2 ml. of a glycylglycine buffer at pH 7.8. The buffered suspension is then injected into the reaction chamber. The apparatus recorded a response of 500 mv.

EXAMPLE 15

The process of Example 13 is repeated except that before testing, the cell broth culture is exposed to 2% aqueous Lysol for about 5 hours. (Lysol contains soap, orthohydroxydiphenyl, alcohol, pine oil, propylene glycol and glycerol.) The Lysol is then removed by centrifuging the cells. The cells are washed 5 more times to remove traces of Lysol, resuspended in deionized water, heated for 15 minutes in a boiling water bath, and 0.1 ml. of the sample injected into the reaction chamber. The apparatus recorded no response indicating that no living organisms are present. The effectiveness of the disinfectant is thereby established.

EXAMPLE 16

A soil extract is prepared by adding approximately 500 mg. of garden soil to 2 ml. of sterile, distilled water. After standing for 20 minutes at room temperature, the mixture is centrifuged for one minute at 1700 G and 0.1 ml. of the fairly clear supernatant is assayed by the method described in Procedure A, above. The apparatus recorded a response of greater than 450 mv. indicating a large microbial population in the soil extract.

EXAMPLE 17

One gram of dry yeast is suspended in 5 ml. of water and shaken. One tenth ml. of the supernatant is tested and a response of 4400 mv. recorded.

EXAMPLE 18

Twenty-two mg. of lyophilized *Serratia marcescens* were suspended in 0.44 ml. of deionized water. The suspension is heated in a boiling water bath for 5 minutes and 0.1 ml. is tested. The apparatus recorded a response of 210 mv.

EXAMPLE 19

A suspension of *Bacillus subtilis* spores (0.1 ml.) is incubated in yeast-dextrose broth at 37°C for 1½ hours. The sample is then tested and a response of 250 mv. is recorded.

EXAMPLE 20

One ml. of washed cells of *Saccharomyces cerevisiae* is added to 10 ml. of acetone. After standing about 1 minute, a 1 ml. aliquot of the mixture is dried and the residue is suspended in 1 ml. of deionized water. The sample (which contains about 37,000 cells) is assayed and a response of 260 mv. is recorded.

EXAMPLE 21

One ml. of a *S. marcescens* cell suspension is added to 10 ml. of a 30% aqueous solution of dimethyl sulfoxide. After standing for 5 minutes, the mixture is assayed by adding 0.1 ml. of treated cell suspension containing extract from about $10^6$ cells to 1.5 ml. of firefly lantern extract. A response of about 3200 mv. is recorded.

EXAMPLE 22

A 5 ml. suspension of *S. marcescens* cells is subjected to 5 minutes of ultrasonic oscillation. After cooling the tube of suspension in flowing water, the suspension is assayed by adding 0.1 ml. of sonically treated cell suspension to 1.5 ml. of firefly lantern extract. A response of 800 mv. is recorded.

EXAMPLE 23

To a 5 ml. suspension of S. marcescens cells there is added 0.1 ml. of perchloric acid. A sample of the mixture is assayed and a response of about 170 mv. recorded.

The overall sensitivity and perhaps reliability of the bioluminescent reaction of the material to be tested may be increased by the conversion of other nucleotide phoshates which are omnipresent in living organisms, such as adenosine diphosphate (ADP) and adenosine monophosphate (AMP), to ATP. This may be accomplished by the utilization of certain phosphorylating enzymes. One such enzyme is phosphocreatine kinase.

The following examples illustrate the use of phosphocreatine kinase to increase the sensitivity of the bioluminescent reaction:

EXAMPLES 24 to 27

Phosphocreatine kinase (10–30 units/mg.) is made up to a concentration of 0.4 mg./ml., in 0.05 M potassium arsenate buffer (pH 7.4) containing $MgSO_4$ at a concentration of $10^{-5}$ M and creatine phosphate at a concentration of 0.1 mg./ml. Four ml. of a S. marcescens cell suspension are subjected to sonic disruption for 5 minutes and then boiled for 5 minutes. After cooling, an aliquot equivalent to 2 million cells is removed for assay. One tenth ml. of the phosphocreatine kinase solution is added to the remainder and allowed to stand for 5 minutes after which it is boiled for 2 minutes. At the end of 5 minutes, another aliquot equivalent to the first is removed and boiled 2 minutes for assay. The remainder is allowed to incubate for an additional 10 minutes after which another aliquot is removed and boiled 2 minutes. A fourth and final aliquot is removed 15 minutes later and boiled 2 minutes. All aliquots are assayed by adding 0.1 ml. of the aliquot to 1.5 ml. of firefly lantern extract (10 mg. extract per ml. of solution). The results are set forth in the following Table.

TABLE

| Example | Incubation Time With Phosphocreatine Kinase | Response (Light Units) |
|---|---|---|
| 24 | 0 | 700 mv. |
| 25 | 5 min. | 4,200 mv. |
| 26 | 15 min. | 18,000 mv. |
| 27 | 30 min. | 20,000 mv. |

Although the use of this precursor conversion modification involves a longer period of time for the assay, its contribution to greater sensitivity is readily apparent.

The following examples illustrate the detection of the presence of bacterial cells and the determination of a specific bacteria by the selection of an appropriate incubation media and environment:

EXAMPLE 28

One ml. of water which is suspected to contain *E. coli* is introduced into 5 ml. of MacConkey broth and the mixture is assayed for ATP content. The mixture is then incubated for several hours, at 44°C. and again assayed. The incubated sample is found to register a significantly higher bioluminescent response than the unincubated sample. The presence of *E. coli* in the sample is thus confirmed.

EXAMPLE 29

Ten ml. portions of nutrient broth containing a different one of each of the following antibiotics in concentrations of 0.5, 1, 2.5 and 5.0 ug./ml. are prepared: Penicillin G, Neomycin and Chloramphenicol. To each broth portion, there is added an equal amount of an aqueous suspension of a bacteria culture obtained from a throat swabbing. Each portion of broth is then incubated. Each broth is assayed for ATP content before and after incubation. It is found that the ATP content of the broth containing 5.0 ug./ml. of Pencillin G has increased less than that of the broths containing the other antibiotics. It is thus established that Penicillin G in a concentration of 5.0 ug./ml. is the most effective antibiotic in treating the bacterial infection.

EXAMPLE 30

Two 10 ml. portions of nutrient broth are prepared, one portion containing typhoid fever antibodies and the other portion containing *staphylococcus* antibodies. Each broth portion is inoculated with equal aliquots of an aqueous suspension of a bacteria culture and incubated. Both before and after incubation, each culture is assayed for ATP content. It is found that the ATP content of the broth containing the *staphylococcus* antibodies increases much less than the ATP content of the broth containing the typhoid fever antibodies, thus indicating that the bacteria present is *staphylococcus*.

I claim:

1. A method for testing an unknown sample of material, said sample containing substantially no adenosine triphosphate which is not in living microorganisms therein, and said material being suspected to contain living microorganisms which comprises:
   a. treating said sample to render adenosine triphosphate in any living microorganisms present therein available for reaction,
   b. contacting said sample with an adenosine triphosphate-reactive mixture comprising luciferin, luciferase, and a cation in the presence of oxygen, and
   c. measuring the light emission from any ensuing reaction, said light emission being indicative of the presence and amount of living microorganisms in said sample.

2. A method of claim 1 wherein said microorganisms are bacteria.

3. A method of claim 1 wherein the sample comprises a solid material and the treatment of said sample includes the step of forming an aqueous suspension of said solid material.

4. A method of claim 1 wherein the treatment of said sample includes the step of reacting said sample with a phosphorylating enzyme to convert any adenosine triphosphate precursors which are present to adenosine triphosphate prior to measuring light emission.

5. A method of claim 1 wherein the treatment of said sample includes the step of extracting adenosine triphosphate present in said microorganisms from said microorganisms.

6. A method of claim 5 wherein the extraction is with dimethylsulfoxide.

7. A method of claim 5 wherein the extraction is with perchloric acid.

8. A method of claim 5 including the step of ultrasonic cell disruption.

9. A method of claim 1 wherein said cation is magnesium.

10. A method of claim 1 wherein adenosine triphosphate which is not in living microorganisms is removed from said sample prior to step (a).

11. A method of claim 10 wherein removal is by washing.

12. A method of claim 10 wherein removal is by centrifuging.

13. A method for testing an unknown sample of material, said sample containing substantially no adenosine triphosphate which is not in living microorganisms therein, and said material being suspected to contain living microorganisms which comprises:
  a. treating said sample to render adenosine triphosphate in any living microorganisms present therein available for reaction,
  b. contacting said sample with an adenosine triphosphate-reactive mixture comprising luciferin, luciferase, and a cation in the presence of oxygen, and
  c. measuring the light emission from any ensuing reaction, said light emission being indicative of the presence and amount of living microorganisms in said sample,
  said method including the step of incubating a second such approximately equal sample of said material in a nutrient medium, repeating the process of steps (a), (b), and (c) on said incubated sample, and comparing the light emission produced by the unincubated sample with that produced by the incubated sample, the presence of living microorganisms in said material being indicated by emission of light in the initial test and confirmed by an increase in light emission produced by said incubated sample over that produced by said unincubated sample.

14. A method of claim 13 for detecting the presence of a specific type of living microorganism suspected to be present in an unknown sample of material wherein said incubation is in a nutrient medium and under conditions favorable to the growth of said suspected type of microorganism, the presence of said suspected type of living microorganism being indicated by an increase in light emission produced by said incubated sample over that produced by said unincubated sample.

15. A method of claim 13 wherein adenosine triphosphate which is not in living microorganisms is removed prior to step (a).

16. A method claim 15 wherein removal is by washing.

17. A method of claim 1 for identifying the type of antibiotic effective for treatment of living microorganisms suspected to be present in an unknown sample of material which includes the steps of providing a plurality of equal aliquots of a nutrient broth for living microorganisms suspected to exist in said sample, adding a different antibiotic to separate aliquots, introducing equal portions of said sample into said aliquots, and incubating said separate aliquots, test steps (a), (b), and (c) being applied to aliquots initially and after incubation, the presence of living microorganisms in said material being indicated by emission of light by an aliquot in said initial test, and the effectiveness of a particular antibiotic being indicated by failure of an incubated aliquot to exhibit a significant increase in light emission after incubation as compared with an aliquot which produced light emission in the initial test.

18. A method of claim 1 for identifying the type of living microorganism suspected to be present in an unknown sample of material which includes the steps of providing a plurality of equal aliquots of a nutrient broth for living microorganisms suspected to exist in said sample, adding a different antibody to each of separate aliquots, said antibodies being specific for different microorganisms, introducing equal portions of said sample into said aliquots, and incubating said separate aliquots, test steps (a), (b), and (c) being applied to aliquots initially and after incubation, the presence of living microorganisms in said material being indicated by emission of light by an aliquot in said initial test and failure of a particular incubated aliquot to exhibit a significant increase in light emission after incubation, as compared with an aliquot which produced light emission in the initial test, being indicative that the antibody contained in that incubated aliquot is specific for microorganisms contained in said material.

* * * * *